US012765931B2

(12) United States Patent
Mason et al.

(10) Patent No.: US 12,765,931 B2
(45) Date of Patent: Oct. 20, 2026

(54) ORTHOPAEDIC SURGICAL INSTRUMENTS FOR DIRECT ANTERIOR APPROACH HIP ARTHROPLASTY AND METHODS OF USE

(71) Applicant: DEPUY IRELAND UNLIMITED COMPANY, Ringaskiddy (IE)

(72) Inventors: John Bohannon Mason, Charlotte, NC (US); James Anderson, Leeds (GB); Ghulam Murtza Khokhar, Cheadle (GB)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 820 days.

(21) Appl. No.: 18/087,760

(22) Filed: Dec. 22, 2022

(65) Prior Publication Data

US 2023/0200874 A1 Jun. 29, 2023

Related U.S. Application Data

(60) Provisional application No. 63/293,636, filed on Dec. 23, 2021.

(51) Int. Cl.

*A61B 17/88* (2006.01)
*A61F 2/30* (2006.01)
*A61F 2/46* (2006.01)

(52) U.S. Cl.

CPC ...... *A61B 17/8808* (2013.01); *A61B 17/8811* (2013.01); *A61B 17/8816* (2013.01);
(Continued)

(58) Field of Classification Search

CPC ............ A61B 17/8802; A61B 17/8805; A61B 17/8808; A61B 17/8811; A61B 17/8816;
(Continued)

(56) References Cited

U.S. PATENT DOCUMENTS 4,293,962 A 10/1981 Fuson
4,815,454 A * 3/1989 Dozier, Jr. ......... A61B 17/8808
606/94
(Continued)

FOREIGN PATENT DOCUMENTS

IN 202111011479 A 4/2021
WO 2021130372 A1 7/2021

OTHER PUBLICATIONS

Depuy Synthes, C-STEM AMT Surgical Technique, 2020, 24 pages.
Depuy Synthes, Actis Total Hip System Surgical Technique, 2021, 20 pages.

*Primary Examiner* — Larry E Waggle, Jr.
(74) *Attorney, Agent, or Firm* — Barnes & Thornburg LLP

(57) ABSTRACT

Orthopaedic instruments for use in a direct anterior approach orthopaedic surgical hip replacement procedure on a patient's femur are disclosed. One such orthopaedic instrument may be embodied as a cement nozzle sized for insertion in a medullary canal of the patient's femur. The cement nozzle may include a first lumen for introducing a bone cement composition into the medullary canal. The cement nozzle may also include a second lumen for removing one or more bodily fluids from the medullary canal during introduction of the bone cement composition. The first and second lumens may each be curved along a distal portion of the cement nozzle.

6 Claims, 5 Drawing Sheets

(52) U.S. Cl.
CPC ...... *A61B 17/8827* (2013.01); *A61F 2/30723* (2013.01); *A61F 2/4601* (2013.01)

(58) Field of Classification Search
CPC . A61B 17/8827; A61F 2/30723; A61F 2/4601
See application file for complete search history.

(56) References Cited

U.S. PATENT DOCUMENTS

| | | | | | |
|---|---|---|---|---|---|
| 4,896,662 | A * | 1/1990 | Noble | A61B 17/8808 | 606/92 |
| 5,741,265 | A * | 4/1998 | Chan | A61B 17/8808 | 606/92 |
| 5,800,439 | A * | 9/1998 | Clyburn | A61B 17/8822 | 606/93 |
| 6,017,350 | A * | 1/2000 | Long | A61B 17/8808 | 606/94 |
| 8,357,168 | B2 * | 1/2013 | Wilson | A61F 2/4611 | 606/92 |
| 10,888,363 | B2 * | 1/2021 | Greenhalgh | A61B 17/7098 | |
| 2006/0089655 | A1 * | 4/2006 | Watkins | A61B 17/8805 | 606/92 |
| 2007/0016216 | A1 * | 1/2007 | Tague | A61B 17/8808 | 606/94 |
| 2023/0019406 | A1 * | 1/2023 | Reves | A61B 17/8811 | |

* cited by examiner

ORTHOPAEDIC SURGICAL INSTRUMENTS FOR DIRECT ANTERIOR APPROACH HIP ARTHROPLASTY AND METHODS OF USE

CROSS-REFERENCE TO RELATED APPLICATION

This application claims priority to and the benefit of U.S. Provisional Patent Application No. 63/293,636, filed Dec. 23, 2021, the entirety of which is incorporated by reference herein.

TECHNICAL FIELD

The present disclosure relates generally to orthopaedic instruments, and particularly to orthopaedic instruments for use in hip replacement surgery.

BACKGROUND

Joint arthroplasty is a well-known surgical procedure by which a diseased and/or damaged natural joint is replaced by a prosthetic joint. The prosthetic joint may include a prosthesis that is implanted into one or more of the patient's bones. Many hip prostheses include a femoral prosthesis that is implanted into a patient's femur. A femoral prosthesis typically includes an elongated stem component that is cemented in the medullary canal of the patient's femur and a spherically-shaped head component that bears against the patient's acetabulum or a prosthetic replacement acetabular cup.

Most bone cements include a self-curing resin formed from the on-site blending of two or more components (e.g., a liquid monomer or co-monomer with a powdered polymer or copolymer). During a hip replacement procedure, after the bone cement composition has been mixed but before it has set, the surgeon fills the medullary canal of the patient's femur with the bone cement composition and then inserts the elongated stem component of the femoral prosthesis into the medullary canal. For improved results, the medullary canal should be relatively free of blood and tissue while the surgeon is introducing the bone cement composition.

Some hip replacement procedures are performed using a direct anterior approach. When using the direct anterior approach, the surgeon does not have line-of-sight access to the medullary canal of the patient's femur. This limited access and visibility makes it difficult for the surgeon to apply the bone cement composition using instruments designed for other approaches (e.g., a posterior approach) and to monitor the composition for contamination during application.

SUMMARY

According to one aspect, an orthopaedic instrument for use in a direct anterior approach orthopaedic surgical hip replacement procedure on a patient's femur may comprise a cement nozzle sized for insertion in a medullary canal of the patient's femur. The cement nozzle may comprise a first lumen for introducing a bone cement composition into the medullary canal. The cement nozzle may also comprise a second lumen for removing one or more bodily fluids from the medullary canal during introduction of the bone cement composition. The first and second lumens may each be curved along a distal portion of the cement nozzle.

In some embodiments, a curvature of the first and second lumens along the distal portion of the cement nozzle may be between 30 and 60 degrees.

In some embodiments, the cement nozzle may comprise a first cannula defining the first lumen. The cement nozzle may also comprise a second cannula at least partially defining the second lumen. A central axis of the second lumen may be spaced apart from a central axis of the first lumen. The central axis of the second lumen may run parallel to the central axis of the first lumen along the distal portion of the cement nozzle. In other embodiments, the second cannula may be disposed around the first cannula along the distal portion of the cement nozzle, such that the second lumen is defined between the first and second cannulas along the distal portion of the cement nozzle.

In some embodiments, a distal end of the first cannula may comprise a flared section having different first and second internal diameters. The second internal diameter may be larger than and positioned distally of the first internal diameter. The second internal diameter may be 25 to 75 percent larger than the first internal diameter. The first internal diameter may be between 6 and 10 millimeters, and the second internal diameter may be between 8 and 16 millimeters.

In some embodiments, the second cannula may include a plurality of fenestrations along the distal portion of the cement nozzle. The plurality of fenestrations may be sized to permit the one or more bodily fluids to flow from the medullary canal into the second lumen. The plurality of fenestrations may also be sized to permit fatty tissue to flow from the medullary canal into the second lumen. A density of the plurality of fenestrations may increase in a proximal-to-distal direction along the second cannula.

In some embodiments, the first cannula may comprise a notch to facilitate separation of the distal portion of the cement nozzle from a proximal portion of the cement nozzle. The first cannula may comprise a collar configured to contact a pressurizer received on the first cannula after separation of the distal and proximal portions of the cement nozzle.

According to another aspect, an orthopaedic instrument for use in a direct anterior approach orthopaedic surgical hip replacement procedure on a patient's femur may comprise a pressurizer configured to seal a proximal end of a medullary canal of the patient's femur when at least partially inserted into the proximal end of the medullary canal after the patient's femur has been proximally resected. The pressurizer may be formed to include an upper surface configured to extend generally parallel to a resected surface of the femur when the pressurizer is at least partially inserted into the proximal end of the medullary canal. The pressurizer may also be formed to include a lower surface opposite the upper surface and configured to be inserted into the proximal end of the medullary canal. The pressurizer may also be formed to include an interior passageway extending between the upper and lower surfaces. The interior passageway may be sized to receive a cement nozzle for adding bone cement composition into the medullary canal while the pressurizer seals the proximal end of a medullary canal. The interior passageway may be disposed at an angle relative to the lower surface of the pressurizer.

In some embodiments, the angle may be between 0 and 25 degrees. The interior passageway may be angled medially relative to the lower surface of the pressurizer. In other embodiments, the interior passageway may be angled laterally relative to the lower surface of the pressurizer.

According to yet another aspect, a method of surgically preparing a patient's femur to receive a prosthesis during a direct anterior approach orthopaedic surgical hip replacement procedure may comprise resecting a proximal end of the patient's femur to expose a medullary canal of the patient's femur. The method may further comprise inserting a distal portion of a cement nozzle into a proximal end of the medullary canal. The method may further comprise delivering a bone cement composition into the medullary canal via the cement nozzle. The method may further comprise, after the distal portion of the cement nozzle has been removed from the medullary canal, separating the distal portion of the cement nozzle from a proximal portion of the cement nozzle. The method may further comprise inserting the proximal portion of the cement nozzle into an interior passageway formed in a pressurizer. The method may further comprise at least partially inserting the pressurizer into the proximal end of the medullary canal to seal the proximal end of a medullary canal. The method may further comprise delivering additional bone cement composition into the medullary canal via the proximal portion of the cement nozzle while the pressurizer seals the proximal end of a medullary canal.

In some embodiments, the distal portion of the cement nozzle may be curved. Inserting the distal portion of a cement nozzle into the proximal end of the medullary canal may comprise inserting the distal portion of the cement nozzle from a medial side of the patient's femur.

In some embodiments, at least partially inserting the pressurizer into the proximal end of the medullary canal to seal the proximal end of a medullary canal may comprise pressing a collar on the proximal portion of the cement nozzle against an upper surface of the pressurizer.

BRIEF DESCRIPTION OF THE DRAWINGS

The detailed description particularly refers to the following figures, in which.

DETAILED DESCRIPTION OF THE DRAWINGS

Figures 1, 2:
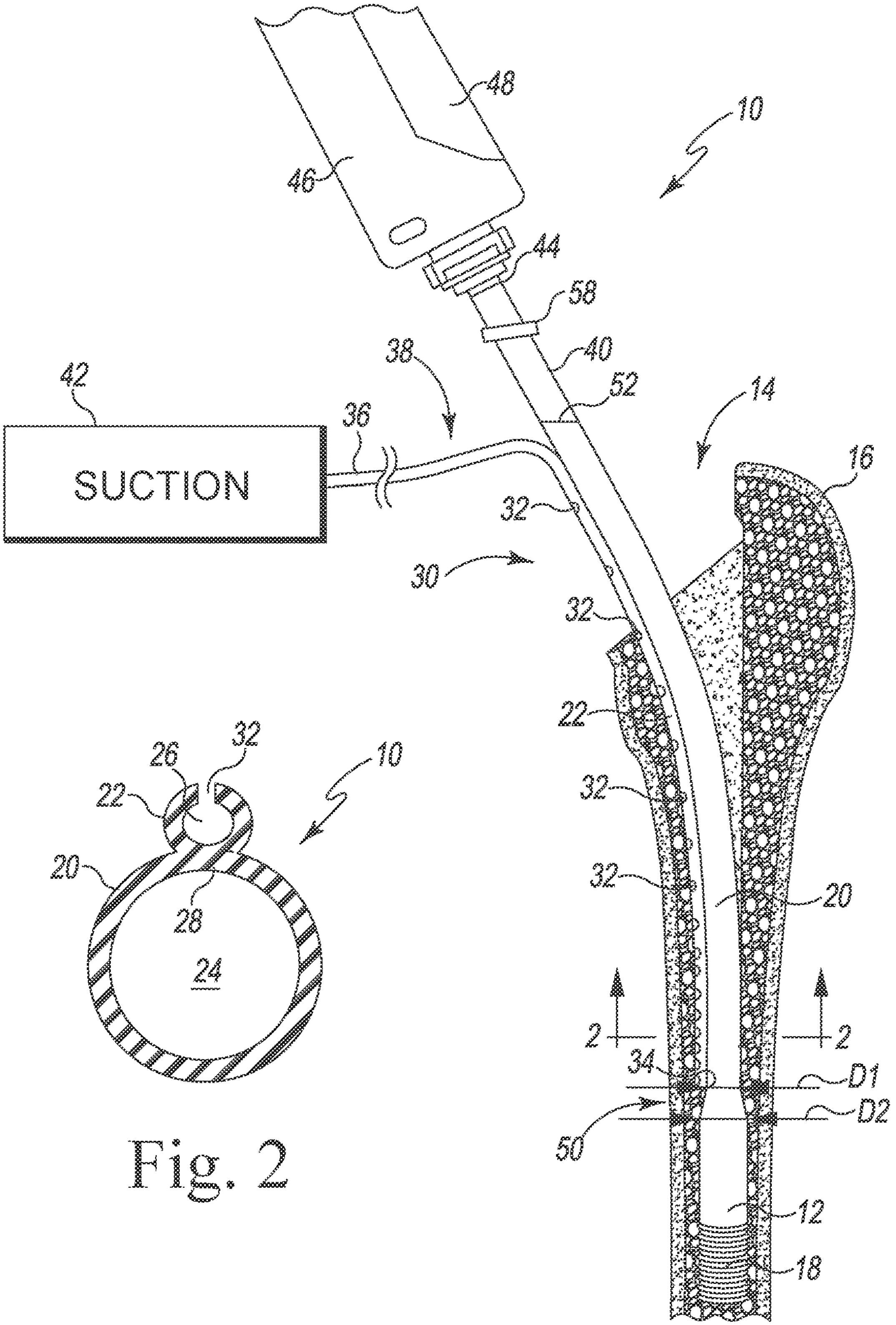
FIG. 1 is a cross-sectional view of a patient's femur during a direct anterior approach hip arthroplasty, showing a surgeon introducing a bone cement composition using a dual lumen cement nozzle according to an one illustrative embodiment of the present disclosure.
FIG. 2 is a cross-sectional view of the dual lumen cement nozzle of FIG. 1, taken along the line 2-2 from FIG. 1.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Referring to FIG. 1, an orthopaedic instrument is illustratively embodied as a dual lumen cement nozzle 10. Specifically, FIG. 1 illustrates the cement nozzle 10 being used to introduce a bone cement composition 12 into a medullary canal 14 of a patient's femur 16 during a direct anterior approach hip arthroplasty. As suggested by FIG. 1, the cement nozzle 10 is sized for insertion in the medullary canal 14.

The cement nozzle 10 includes two cannulas 20, 22. As discussed further below, the cannula 20 defines a lumen 24 sized for introducing the bone cement composition 12 into the medullary canal 14, and the cannula 22 defines a lumen 26 sized for removing one or more bodily fluids (e.g., blood) from the medullary canal 14 during the introduction of the bone cement composition 12. In some embodiments, the lumen 26 may also be sized for removing one or more bodily tissues (e.g., fatty tissue) from the medullary canal 14 during the introduction of the bone cement composition 12.

To facilitate a direct anterior approach hip arthroplasty, the lumens 24, 26 are each curved along a distal portion 30 of the cement nozzle 10. This curvature allows a surgeon to insert the cement nozzle 10 in the medullary canal 14 of the patient's femur 16 despite not having line-of-sight access to the medullary canal 14. In particular, the surgeon insert the cement nozzle 10 in the medullary canal 14 from a medial side of the patient's femur 16 that is exposed during the direct anterior approach hip arthroplasty.

The curvature of the lumens 24, 26 along the distal portion 30 of the cement nozzle 10 is between 0 and 90 degrees. In some embodiments, this curvature of the lumens 24, 26 is between 10 and 80 degrees, between 20 and 70 degrees, between 30 and 60 degrees, or between 40 and 50 degrees. In one embodiment, this curvature of the lumens 24, 26 is about 45 degrees. It should also be appreciated that the cannulas 20, 22 may be flexible, such that that the curvature of the lumens 24, 26 can change during use of the cement nozzle 10. By way of example, the cannulas 20, 22 may be made of plastic with a wall thickness between 0.5 and 1 millimeters, such that the cannulas 20, 22 can bend during use.

As shown in FIG. 1, the lumens 24, 26 extend parallel to one another along the distal portion 30 of the cement nozzle 10. In the illustrative embodiment, the cannulas 20, 22 each form part of one integral component made by injection-molding plastic. In this embodiment, the cannulas 20, 22 share a common wall 28, as best seen in FIG. 2 (a cross-sectional view of the cement nozzle 10 taken along the line 2-2 from FIG. 1). In one alternative embodiment, the cannulas 20, 22 may be distinct components that are coupled together (e.g., using an adhesive) along the distal portion 30 of the cement nozzle 10.

The cannula 22 includes fenestrations 32 (only some of which are labeled in FIG. 1 for clarity), which are sized to permit one or more bodily fluids (e.g., blood) to flow from the medullary canal 14 into the second lumen 28. In some embodiments, the fenestrations may also be sized to permit one or more bodily tissues (e.g., fatty tissue) to flow from the medullary canal 14 into the second lumen 28. As shown in FIG. 1, in the illustrative embodiment, the density of the fenestrations 32 increases in a proximal-to-distal direction along the cannula 22. In other words, spacing between fenestrations 32 nearer a distal end 34 of the cannula 22 is less than spacing between fenestrations 34 nearer a proximal end 36 of the cannula.

As illustrated in FIG. 1, a proximal section 38 of the cannula 22 is separate from a proximal section 40 of the cannula 40, such that the proximal end 36 of the cannula 22 can be coupled to a source of suction 40. The suction source 42 creates negative pressure in the lumen 26, so that bodily fluids and/or tissues present in the medullary canal 14 can be sucked through the fenestrations 32 and up through the lumen 26. The multiple fenestrations 32 spaced along the cannula 22 maintain suction even if the distal end 34 of the cannula 22 becomes submerged in bone cement composition 12 during use.

A proximal end 44 of the cannula 20 is configured to couple to a cement gun 46 to receive the bone cement composition 12. During use, the bone cement composition 12 is mixed using an appropriate mixing system and filled into a delivery syringe 48 that is attached to the cement gun 46. The surgeon then inserts the cement nozzle 10 into the medullary canal 14 until the cement nozzle is adjacent a cement restrictor 18 (previously installed by the surgeon). The surgeon then activates the cement gun 46 (e.g., by pulling a trigger) to cause the bone cement composition 12 to flow from the delivery syringe 48 through the lumen 24 and into the medullary canal 14. The surgeon continues to introduce the bone cement composition 12 into the medullary canal 14 in a retrograde fashion, allowing the bone cement composition 12 to push the cement nozzle 10 gently back, until the medullary canal 14 is completely filled (see FIG. 3).

To facilitate this operation, the cannula 20 includes a flared section 50 at its distal end. The flared section 50 improves pressurization of the bone cement composition 12 during its introduction into the medullary canal 14. The flared section 50 also improves haptic feedback for the surgeon operating the cement gun 46, allowing the surgeon to better control the introduction of the bone cement composition 12.

In the flared section 50, the internal diameter of the cannula 20 increases along a proximal-to-distal direction. For example, with reference to FIG. 1, an internal diameter D1 near a proximal end of the flared section 50 is smaller than an internal diameter D2 near a distal end of the flared section 50. In some embodiments, the internal diameter D1 may be between 6 and 10 millimeters, while the internal diameter D2 may be between 8 and 16 millimeters. In some embodiments, the internal diameter D2 may be 25 to 75 percent larger than the internal diameter D1. For example, in one illustrative embodiment, the internal diameter D1 may be 8 millimeters and the internal diameter D2 may be 11 millimeters. It is contemplated that, if the surgeon needs to adjust the distal-most diameter of the cannula 20 (e.g., to fit the cement nozzle 10 into a smaller medullary canal), the surgeon can resect the cannula 20 anywhere along the flared section 50 to decrease its distal-most diameter.

Figures 3, 7:
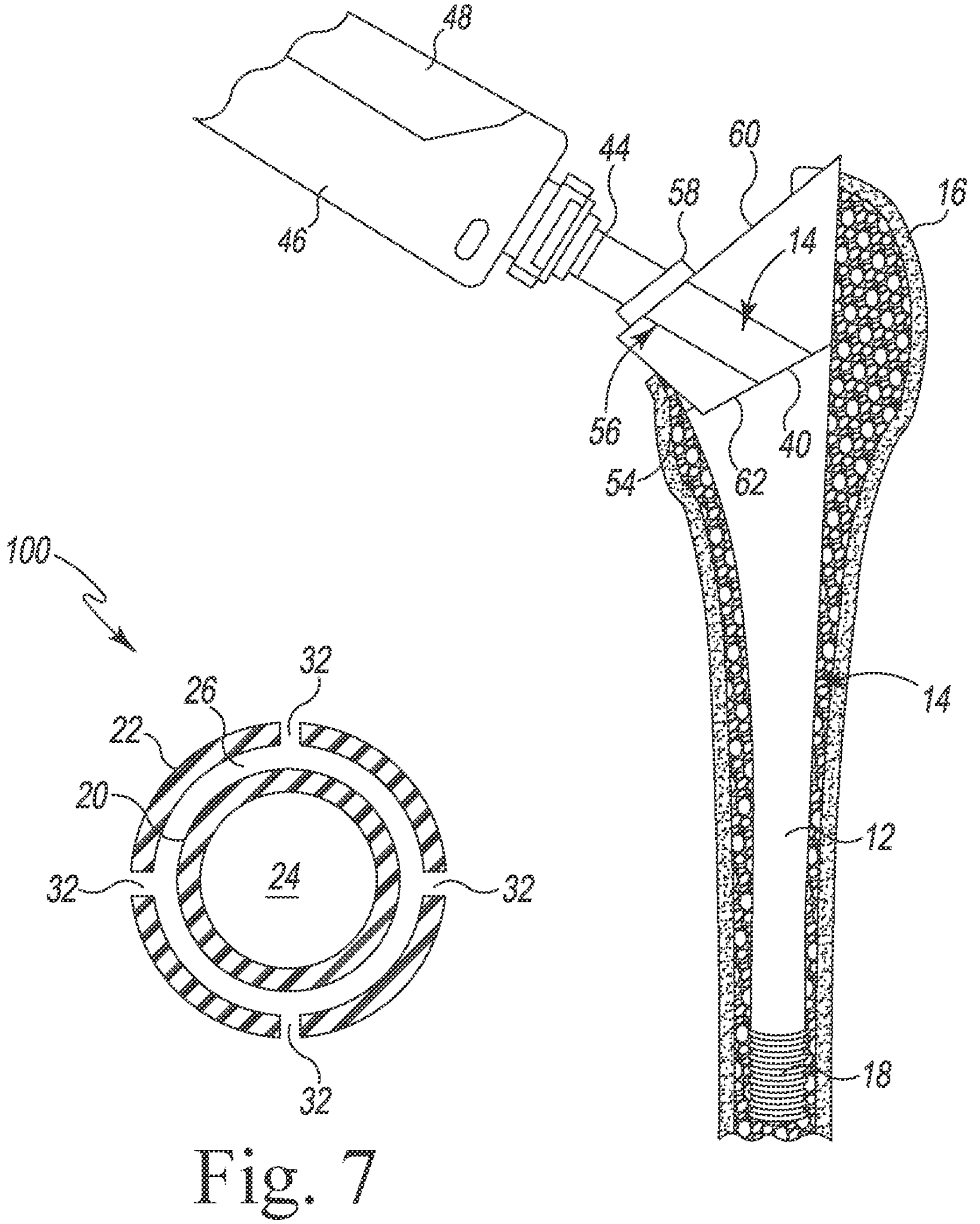
FIG. 3 is another cross-sectional view of the patient's femur during the direct anterior approach hip arthroplasty, showing a surgeon pressurizing the bone cement composition using a femoral pressurizer and a proximal portion of the dual lumen cement nozzle (after removing a distal portion of the dual lumen cement nozzle)
FIG. 7 is a cross-sectional view of a dual lumen cement nozzle according to another illustrative embodiment of the present disclosure.

Referring now to FIG. 3, after the surgeon has filled the medullary canal 14 with the bone cement composition 12, the surgeon pressurizes the bone cement composition 12 to allow good interdigitation of the cement into the trabecular bone. In this part of the procedure, the surgeon separates the distal portion 30 of the cement nozzle 10 from a proximal portion of the cement nozzle (specifically, the proximal section 40 of the cannula 20). In the illustrative embodiment, the cannula 20 includes a notch 52 positioned between the proximal and distal sections of the cannula 20 to facilitate this separation. The notch 52 is scored into the outer diameter of the cannula 20 to decrease the wall thickness. This narrower wall thickness at the notch 52 makes it easier for a surgeon to either tear (by hand) or resect (e.g., using a scalpel) the cannula 20 at the notch 52.

After removing the distal portion 30 of the cement nozzle 10, the surgeon places a femoral pressurizer 54 over the remaining proximal section 40 of the cannula 20. In the illustrative embodiment shown in FIG. 3, the femoral pressurizer 54 is made of silicon and has a generally trapezoidal cross-section with an interior passageway 56 sized to receive the proximal section 40 of the cannula 20. The proximal section 40 of the cannula 20 includes a collar 58 of increased diameter relative to the outer diameter of the rest of the proximal section 40 of the cannula 20. The collar 58 engages an upper surface 60 of the femoral pressurizer 54, such that the collar 58 pushes down on the femoral pressurizer 54 when the surgeon pushes down on the cement gun 46. While engaging the femoral pressurizer 54 with the proximal opening of the medullary canal 14 to seal the medullary canal 14, the surgeon injects additional bone cement composition 12 from the cement gun 46 (e.g., by pulling a trigger of the cement gun 46) to pressurize the bone cement composition 12. The patient's femur 16 is then ready to receive the elongated stem component of a femoral prosthesis.

Figure 4A:
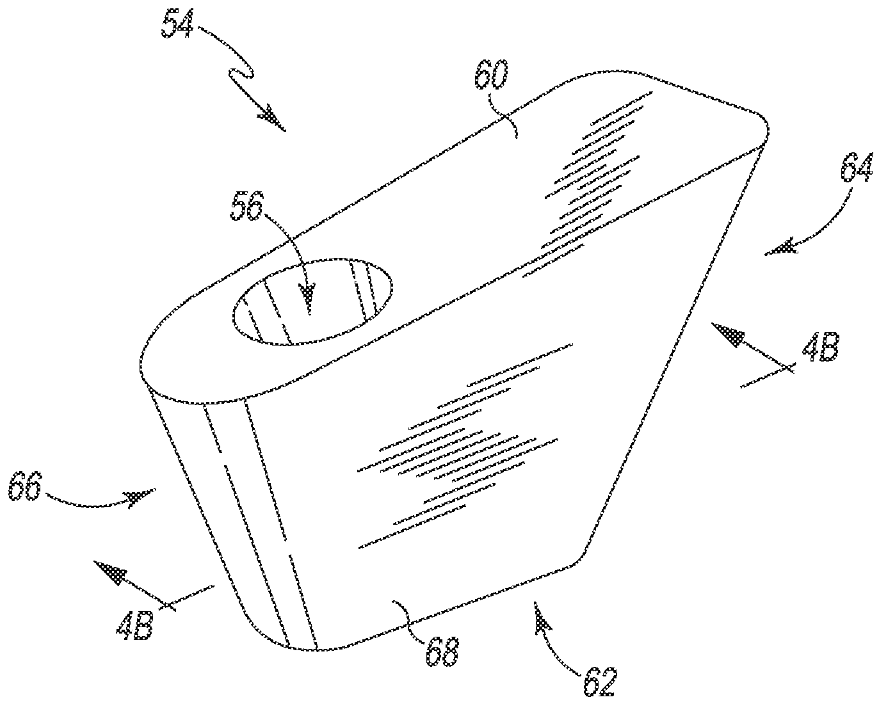
FIG. 4A is a perspective view of the femoral pressurizer of FIG. 3.
Figure 4B:
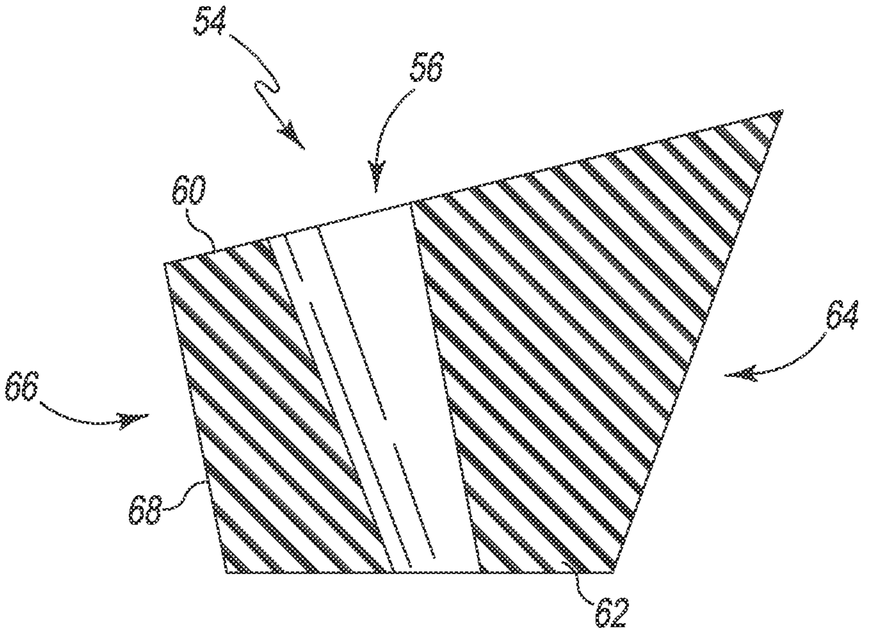
FIG. 4B is a cross-sectional view of the femoral pressurizer of FIGS. 3 and 4A, taken along the line 4B-4B from FIG. 4A.

The pressurizer 54 is shown in additional detail in the perspective view of FIG. 4A and the cross-sectional view of FIG. 4B. The upper surface 60 of the pressurizer 54 is planar and configured to extend generally parallel (i.e., within ±10 degrees of parallel) to the resected surface of the femur 16 when the pressurizer 54 is at least partially inserted into the proximal end of the medullary canal 14 (as suggested by FIG. 3). The femur 16 is typically resected along a plane that angled at about 45-50 degrees with respect to a longitudinal axis of the femur 16. As such, the upper surface 16 is configured to be angled at about 35-60 degrees with respect to the longitudinal axis of the femur 16 when the pressurizer 54 is at least partially inserted into the proximal end of the medullary canal 14.

The pressurizer 54 also includes a lower surface 62 opposite the upper surface 60. As shown in FIG. 3, the lower surface 62 is inserted into the proximal end of the medullary canal 14 in use. In the illustrative embodiment, the lower surface 62 is planar and is disposed at an angle relative to the upper surface 60, such that the upper surface 60 and lower surface 62 are spaced further from one another on a lateral side 64 of the pressurizer 54 than they are on a medial side 66 of the pressurizer 54. For instance, in some embodiments, the angle between the upper surface 60 and lower surface 62 may be between 10-20 degrees, and the lateral side 64 may be about 50 percent taller than the medial side 66.

The pressurizer 54 further includes a side wall 68 that extends between and connects the upper surface 60 and the lower surface 62. The side wall 68 has a shape that is configured to conform to the exposed proximal opening of the medullary canal 14 of the femur 16. In particular, the side wall 68 is rounded on the medial side 66 of the pressurizer 54. The side wall 68 has planar sections on the lateral side 64 as well as anterior and posterior sides of the pressurizer 54. The side wall 68 includes rounded corners between the planar section on the lateral side 64 and each of the planar sections on the anterior and posterior sides of the pressurizer 54. The lower surface 62 is generally smaller in each dimension than the upper surface 60, such that the sidewall tapers inwardly from the upper surface 60 toward the lower surface 62. This tapering promotes an interference fit between the side wall 68 and the exposed proximal opening of the medullary canal 14 when the pressurizer 54 is at least partially inserted.

The interior passageway 56 of the pressurizer 54 extends between the upper surface 60 and the lower surface 62. As discussed above, the passageway 56 is sized to receive a portion of a cement nozzle (e.g., the proximal section 40 of the cannula 20 of the cement nozzle 10). A portion cement nozzle can extend through the passageway 56 and into the medullary canal 14 of the femur 16 when the pressurizer 54 is at least partially inserted into the proximal end of the medullary canal 14. In the illustrative embodiment, as shown in FIG. 4B, a diameter of the passageway 56 where it intersects the lower surface 62 of the pressurizer 54 is smaller than a diameter of the passageway 56 where it intersects the upper surface 60 of the pressurizer 54. This tapering of the passageway 56 from the upper surface 60 toward the lower surface 62 promotes an interference fit with the portion of the cement nozzle 10 that is inserted through the passageway 56 in use.

Figure 5A:
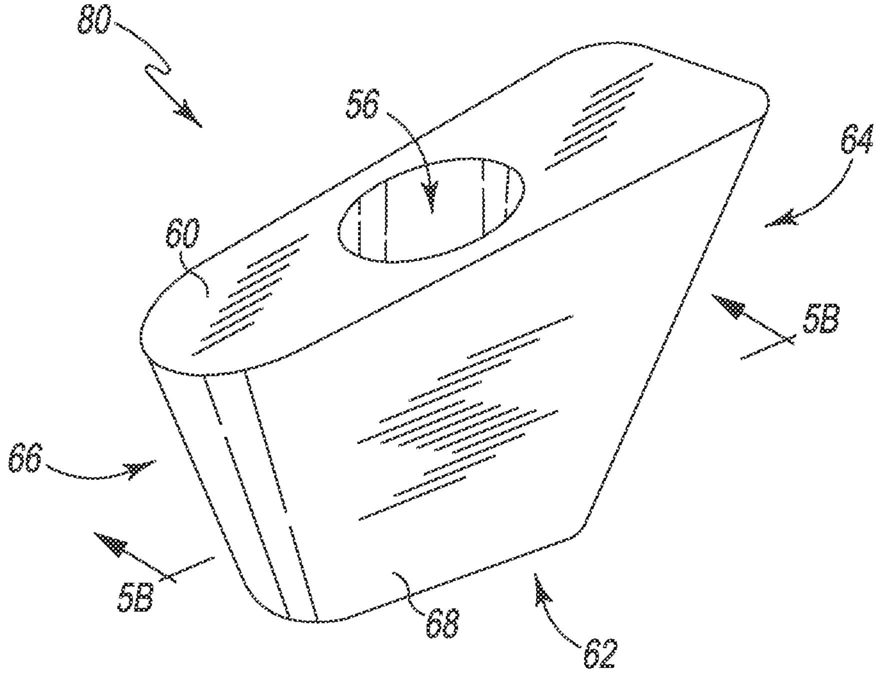
FIG. 5A is a perspective view of a femoral pressurizer according to another illustrative embodiment of the present disclosure.
Figure 5B:
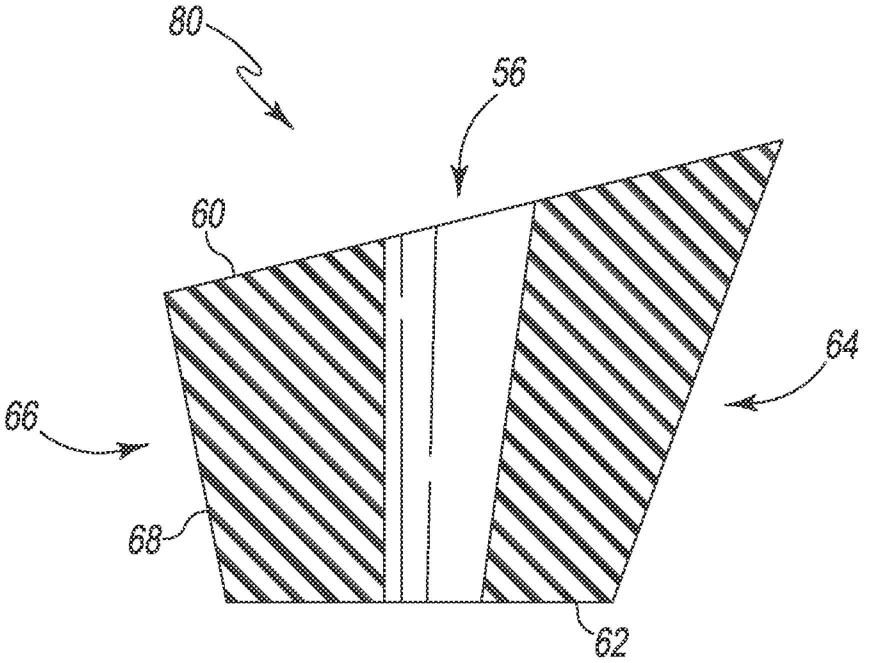
FIG. 5B is a cross-sectional view of the femoral pressurizer of FIG. 5A, taken along the line 5B-5B from FIG. 5A.
Figure 6A:
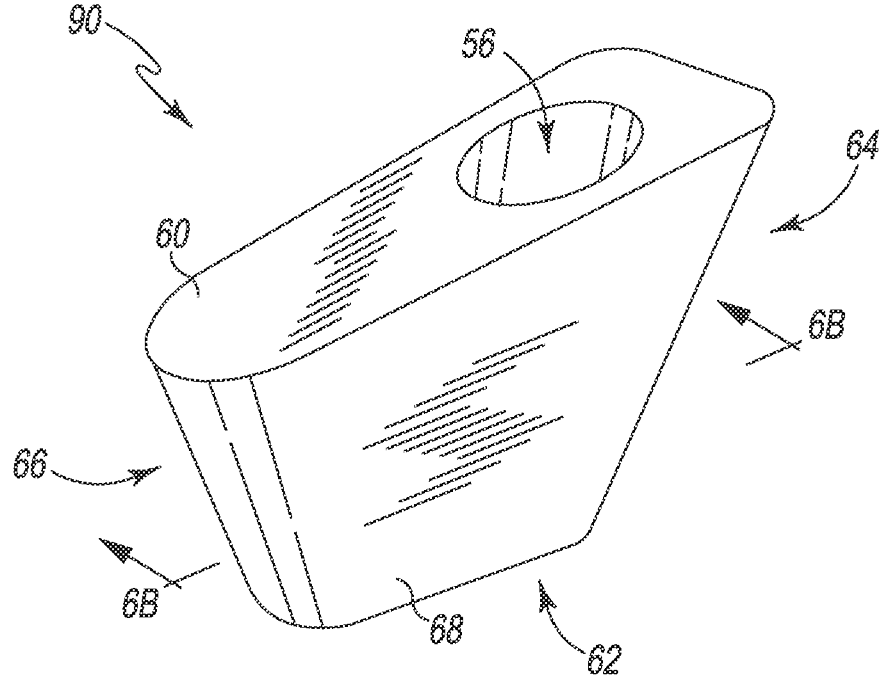
FIG. 6A is a perspective view of a femoral pressurizer according to yet another illustrative embodiment of the present disclosure.
Figure 6B:
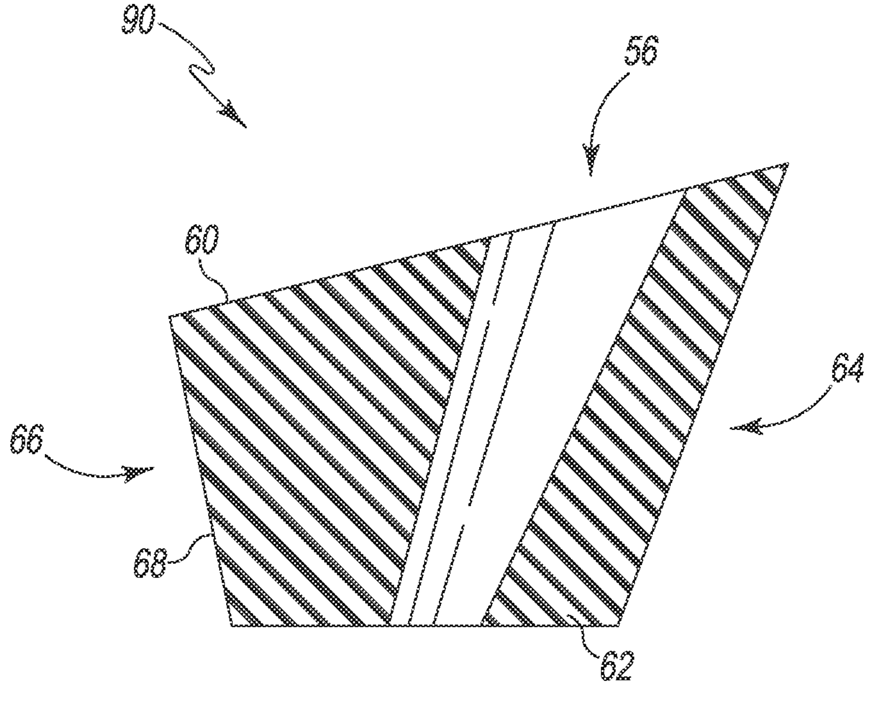
FIG. 6B is a cross-sectional view of the femoral pressurizer of FIG. 6A, taken along the line 6B-6B from FIG. 6A.

In the illustrative embodiment of FIGS. 3, 4A, and 4B, the passageway 56 is disposed at an angle relative to the lower surface 62 of the pressurizer 54. In this embodiment, the passageway 56 is angled medially at about 20 degrees toward the medial side 66 of the pressurizer 54. In an alternative embodiment, shown as pressurizer 80 in FIGS. 6A and 6B, the passageway 56 is angled laterally at about 20 degrees toward the lateral side 64 of the pressurizer 80. It is contemplated that, in other embodiments, the passageway may be disposed at another angle between 0 and 25 degrees relative to the lower surface 62 (either medially or laterally). In another alternative embodiment, shown as pressurizer 90 in FIGS. 5A and 5B, the passageway 56 is disposed perpendicularly to the lower surface 62 of the pressurizer 90. It will be appreciated that each of these different orientations of the passageway 56 in the pressurizers 54, 80, 90 results in the cement nozzle 10 (and, typically, the cement gun 46) being positioned at a different angle relative to the pressurizer 54, 80, 90 and the femur 16 during the pressurization of the bone cement composition 12. Other than the different orientations of the passageway 56, however, the pressurizers 54, 80, 90 are identical. Each of the pressurizers 54, 80, 90 may be produced in different sizes, and possibly with different relative dimensions, to accommodate differently sized femurs 16 and medullary canals 14. An orthopaedic system can include multiple styles and/or sizes of the pressurizers 54, 80, 90 to accommodate different patient needs and/or surgeon preferences.

FIG. 7 illustrates a cross-sectional view of an alternative embodiment of a dual lumen cement nozzle 100 according to the present disclosure (from a similar perspective as FIG. 2). In this embodiment, the lumens 24, 26 are coaxial along the distal portion 30 of the cement nozzle 100. As with the cement nozzle 10, the cannula 20 of cement nozzle 100 also defines the lumen 24 for introducing the bone cement composition 12 into the medullary canal 14. In cement nozzle 100, however, the cannula 22 is disposed around the cannula 20, such that the lumen 26 (for removing one or more bodily fluids and/or tissues from the medullary canal 14) is defined between the cannulas 20, 22, as shown in FIG. 7. In the illustrative embodiment of the cement nozzle 100, the fenestrations 32 are distributed around the circumference of the cannula 22. The structure and operation of the cement nozzle 100 is otherwise similar to the cement nozzle 10 described above.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic instrument for use in a direct anterior approach orthopaedic surgical hip replacement procedure on a patient's femur, the orthopaedic instrument comprising:

a pressurizer configured to seal a proximal end of a medullary canal of the patient's femur when at least partially inserted into the proximal end of the medullary canal after the patient's femur has been proximally resected, wherein the pressurizer is formed to include:

an upper planar surface configured to extend generally parallel to a resected surface of the femur when the pressurizer is at least partially inserted into the proximal end of the medullary canal;

a lower planar surface opposite the upper planar surface and configured to be inserted into the proximal end of the medullary canal;

a sidewall connecting the upper planar surface and the lower planar surface, the sidewall comprising a lateral planar section and a medial rounded section that are configured to conform to the proximal end of the medullary canal; and an interior passageway extending between the upper and lower planar surfaces and sized to receive a cement nozzle for adding bone cement composition into the medullary canal while the pressurizer seals the proximal end of the medullary canal, wherein the interior passageway is disposed at an angle relative to the lower planar surface of the pressurizer, and wherein the angle is between 0 and 25 degrees.

2. The orthopaedic instrument of claim 1, wherein the interior passageway is angled medially relative to the lower planar surface of the pressurizer.

3. The orthopaedic instrument of claim 1, wherein the interior passageway is angled laterally relative to the lower planar surface of the pressurizer.

4. A method of surgically preparing a patient's femur to receive a prosthesis during a direct anterior approach orthopaedic surgical hip replacement procedure, the method comprising:

accessing the patient's femur through a direct anterior incision;

resecting a proximal end of the patient's femur to expose a medullary canal of the patient's femur;

inserting a distal portion of a cement nozzle through the direct anterior incision and into a proximal end of the medullary canal;

delivering a bone cement composition into the medullary canal via the cement nozzle;

removing the distal portion of the cement nozzle from the medullary canal and the direct anterior incision;

after the distal portion of the cement nozzle has been removed from the medullary canal and the direct anterior incision, separating the distal portion of the cement nozzle from a proximal portion of the cement nozzle;

inserting the proximal portion of the cement nozzle into an interior passageway formed in a pressurizer;

at least partially inserting the pressurizer through the direct anterior incision and into the proximal end of the medullary canal to seal the proximal end of the medullary canal; and delivering additional bone cement composition into the medullary canal via the proximal portion of the cement nozzle while the pressurizer seals the proximal end of the medullary canal.

5. The method of claim 4, wherein the distal portion of the cement nozzle is curved, and wherein inserting the distal portion of the cement nozzle through the direct anterior incision and into the proximal end of the medullary canal comprises inserting the distal portion of the cement nozzle from a medial side of the patient's femur.

6. The method of claim 4, wherein at least partially inserting the pressurizer through the direct anterior incision and into the proximal end of the medullary canal to seal the proximal end of the medullary canal comprises pressing a collar on the proximal portion of the cement nozzle against an upper surface of the pressurizer.

* * * * *